United States Patent
Van Den Wildenberg

(10) Patent No.: US 6,342,388 B1
(45) Date of Patent: Jan. 29, 2002

(54) CULTURE MEDIUM CONTAINER, WITH INTEGRATED GEOMETRY FOR AIR SUCTION AND AIR CONDUCTION, FOR THE PURPOSE OF AIR BACTERIA ANALYSIS

(76) Inventor: Pierre Van Den Wildenberg, Oberer Chämletenweg 42a, 6330 Cham (CH)

( * ) Notice: Subject to any disclaimer, the term of this patent is extended or adjusted under 35 U.S.C. 154(b) by 0 days.

(21) Appl. No.: 09/436,049

(22) Filed: Nov. 8, 1999

(30) Foreign Application Priority Data

Nov. 13, 1998 (EP) .............................................. 98811137

(51) Int. Cl.⁷ ................................................ C12M 1/26
(52) U.S. Cl. .............................. 435/287.1; 435/288.3; 435/297.5; 435/309.1; 73/28.05; 73/863.22
(58) Field of Search ........................... 435/287.1, 287.4, 435/287.7, 287.9, 288.3, 288.5, 294.1, 297.5, 305.1, 305.4, 309.1; 73/28.05, 28.06, 863.22

(56) References Cited

U.S. PATENT DOCUMENTS

| | | | |
|---|---|---|---|
| 3,001,914 A | | 9/1961 | Andersen ................. 195/103.5 |
| 3,693,457 A | * | 9/1972 | Pilat |
| 3,795,135 A | | 3/1974 | Andersen ..................... 73/28 |
| 3,938,366 A | | 2/1976 | Wertlake et al. ............... 73/28 |
| 4,038,057 A | * | 7/1977 | Roth |
| 4,640,140 A | * | 2/1987 | Burghoffer et al. |
| 6,040,153 A | * | 3/2000 | Lemonnier |

FOREIGN PATENT DOCUMENTS

| | | |
|---|---|---|
| GB | 1 441 576 | 7/1976 |
| GB | 2 224 118 A | 4/1990 |
| WO | WO 96/31594 | 10/1996 |

* cited by examiner

Primary Examiner—William H. Beisner
(74) Attorney, Agent, or Firm—Seed Intellectual Property Law Group PLLC

(57) ABSTRACT

A container for a culture medium having a dish and a lid, and having an integrated geometry for air suction and air conduction. The container being adapted for analysis of air bacteria according to the impaction method. An adapted cascade connecting hood, which can be disposed between two successive containers, makes possible a cascade-like serial arrangement of a plurality of culture medium containers, which, with suction apertures of differing size, allows a differentiation according to particle size when analyzing air bacteria.

9 Claims, 5 Drawing Sheets

CULTURE MEDIUM CONTAINER, WITH INTEGRATED GEOMETRY FOR AIR SUCTION AND AIR CONDUCTION, FOR THE PURPOSE OF AIR BACTERIA ANALYSIS

TECHNICAL FIELD

This invention relates to culture medium containers for analysis of bacteria.

BACKGROUND OF THE INVENTION

Air bacteria analysis according to the impaction method, in which commercially available petri dishes are used, represents one of the most commonly applied methods. In all applications known so far, the culture medium tub of the petri dish is introduced into a specially constructed suction chamber of the air suction unit. This suction chamber has suction apertures (holes or respectively slits), through which the environmental air is suctioned. As a result of the volume of the airstream and the geometry of the suction apertures, the particles in the airstream are accelerated so much that the air particles strike the underlying surface of the culture medium in the culture medium tub, and are received there.

This method has a system-dependent course, is very time-consuming, and handling is complicated. The petri dish first has to be opened. During the measuring period, the lid must be kept in such a way that no sterilization error occurs. The culture medium tub of the petri dish must be inserted without sterilization errors into the suction chamber of the device. After measurement, the whole thing takes place in reversed order.

Owing to the different filling levels of the culture medium (depending upon the manufacturer), the spacing between the culture medium surface and the air admission plane, of the suction chamber, must be corrected. If this is not done, a measuring mistake can occur.

SUMMARY OF THE INVENTION

The invention presented here has as its object overcoming all these drawbacks.

The invention has, as subject matter, a culture medium container, which is useful for air bacteria analysis in particular according to the impaction method. The culture medium container comprises a dish and a fitted lid, and includes an integrated geometry for air suction and air conduction in the form of apertures in lid and dish.

The culture medium container according to the invention, which is intended for air bacteria analysis according to the impaction method, represents a further development of the petri dish.

The culture medium container comprises a dish or tub and a lid. The two parts are made preferably of injection-molded plastic, e.g., polycarbonate. The dish or tub can be provided with culture medium by the manufacturer or by the user.

The lid is provided with air suction apertures, holes or slits, which have preferably an optimized suction geometry. In one embodiment, a tapered recess is located in the middle of the lid for the purpose of mechanical connection to the dish.

The dish has in the middle a protuberance directed into the dish interior, which protuberance is provided with at least one or more apertures for air outlet. The edge of the protuberance represents a hole directed downward, into which the said apertures come out. The hole has preferably a conical shape, for receiving an air suction device or air suction hose. There is, if necessary, for mechanical connection to the tapered recess of the lid a tapered area in the upper region of the protuberance.

The culture medium containers are normally supplied filled in a sterile way and stacked. For measurement purposes, a container can easily be withdrawn and put directly on an air suction unit or over the hose connection. Afterwards, the measurement takes place in that a defined volume of air, e.g., from 50l up to 1000l, is suctioned in for a certain period of time. The direction of flow of the air is indicated by means of arrows in FIG. 1, FIG. 3 and FIG. 4. After the measurement, the container is removed, stacked in a transportable way, and then incubated. Not until after incubation is the container lid removed for the bacteriological analysis.

In addition to the definition of the invention according to claim 1, special embodiments of the culture medium containers for air bacteria analysis according to the present invention can have the features mentioned in the following, either alone or in a desired combination:

A system-dependent impaction distance within very narrow tolerances (FIGS. 1, 2) between the air admission plane and the culture medium surface.

A mechanically stable connection between the lid and the tub by means of conical plug-in connection.

An airtight and hermetic connection between the lid and the tub, if necessary the sealing being achieved by means of O-ring.

The lid is provided with air suction apertures.

The air suction apertures have an optimized suction geometry.

The air suction apertures can have different aperture sizes.

Different lids with varying aperture sizes should be available so that a differentiation according to particle size is possible.

Adaptation of the culture medium containers for a cascade-like configuration of a plurality of culture medium containers. For this purpose a cascade connecting hood is proposed, which makes possible, by means of O-ring, a hermetic serial configuration of, for example, three culture medium containers over one another, each with a lid of different suction aperture size. This allows a differentiation according to particle size.

All system parts have a mechanical, stable, conical plug-in connection to one another.

The culture medium container lid is provided with a central recess which makes possible a stable conical connection to the dish or to the culture medium tub.

The culture medium dish is preferably provided with a central protuberance, which has on its upper side and on its lower side one connecting socket each, each with a blind hole. The blind hole of the upper connecting socket serves to receive the recess of the lid for the purpose of stable conical connection of the culture medium container lids, while the blind hole in the lower connecting socket optionally serves to receive a connecting peg.

The central protuberance of the culture medium dish has air passages.

The geometry of the recess in the lid and the geometry of the protuberance in the dish allow a plug-in connection by means of the above-mentioned connecting peg for the purpose of stacking a plurality of culture medium containers without cascade hood.

The dimension of the connecting peg can be selected in such a way that, when stacking, an air gap remains between the dish and the lid for the purpose of air exchange during incubation.

The length of the connecting peg can also be selected in such a way that the lid of the dish and the bottom of an adjacent dish are in mutual contact without any gap so that no air exchange is possible.

The protuberance of the dish allows a mechanically stable conical connection to air suction hoses, air suction units, cascade connecting hood, and to the sealing peg.

By means of a simple plug-in connection, the culture medium container can be placed on an air suction-in unit or respectively on an air suction-exhaust unit.

The present invention will be explained more closely by means of the attached FIGS. 1 to 5.

DETAILED DESCRIPTION OF THE ILLUSTRATED EMBODIMENTS

Figure 1:
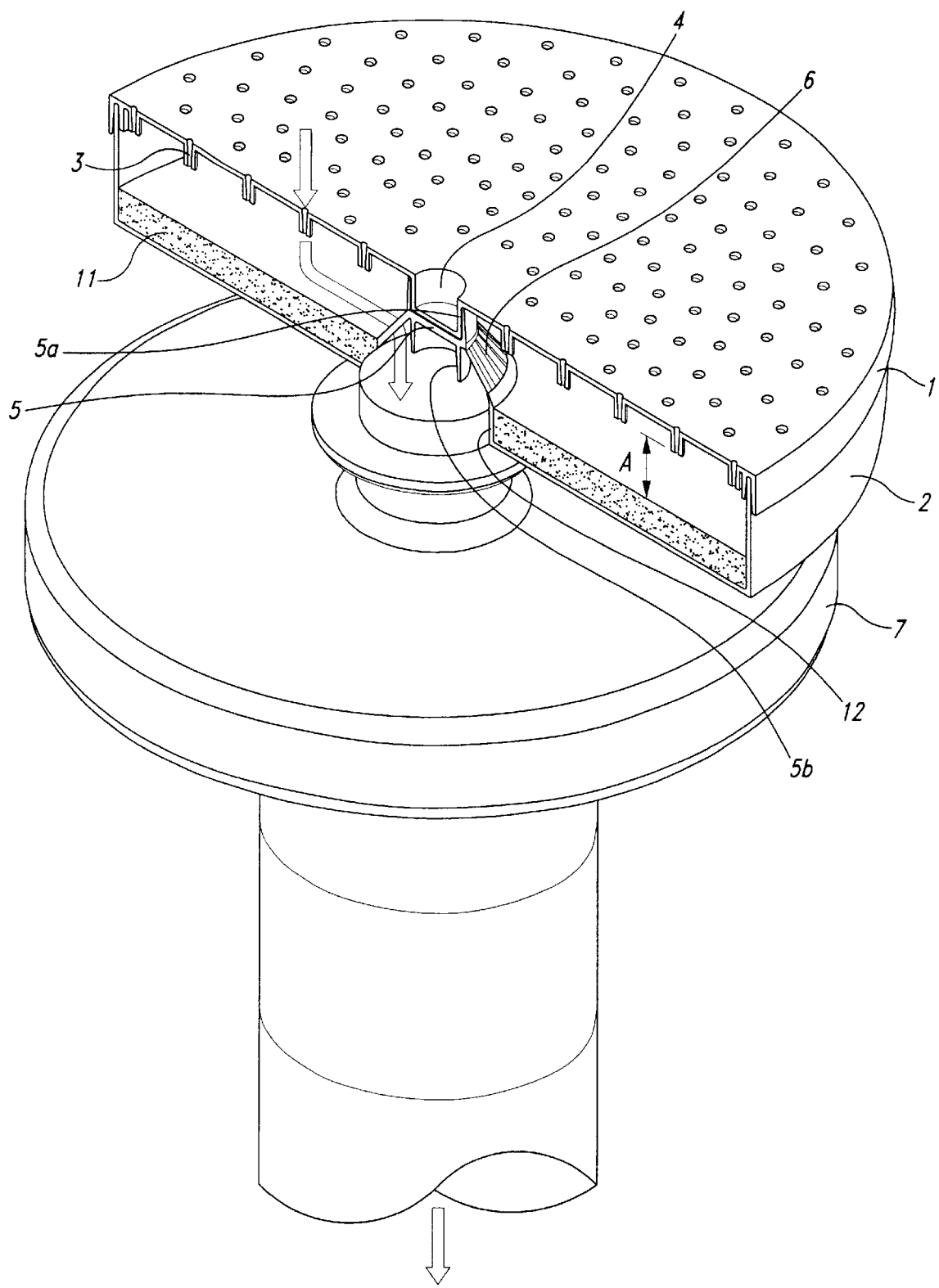
FIG. 1 shows, in perspective, a culture medium container according to the present invention, in section, the container being connected to an air suction device.

Shown in FIG. 1 is a view, in perspective, of a culture medium container according to an embodiment of the present invention, with a section through the central axis, for better clarification. The culture medium container is connected to an air suction device 7, which is responsible for generation of an airstream through the culture medium container. The culture medium container comprises a lid 1, a dish 2 and a culture medium 11. In the middle of the lid 1 there is a recess 4, which has a tapered shape, which fits into a blind hole in the central part 5 of the protuberance 12, which is provided centrally in the interior of the dish 2, this connection being useful for a stable fit of the lid 1. The lid 1 has a multiplicity of regularly disposed air admission apertures 3, which come out into a nozzle, which is directed into the interior of the culture medium container. The spacing of the nozzle of the air admission aperture 3 to the culture medium is constant, and has the value A (impaction distance). The protuberance 12 of the dish 2 directed into the container interior has air outlet slits 6, which are disposed regularly around the central part 5. The central part 5 is provided with an upper connecting socket 5a with blind hole, whose opening is directed upward with respect to the dish interior, and serves to receive the recess 4 of the lid 1.

Constructed on the central part 5, on the dish 2 bottom side, is a lower connecting socket 5b with blind hole. To form plug-in connections, the blind holes can each have a conical shape. The lid 1 forms a hermetic seal with the dish 2, whereby a groove can be provided in the lid for this purpose in which an O-ring 13 (FIG. 2) of corresponding size is situated. When the air suction device 7 is connected to the protuberance 12 of the dish 2, the air suction step begins. A low pressure is thereby generated in the dish interior, air from outside the dish 2 being sucked into the dish interior through the air admission apertures 3. Contained particles are "shot" into the culture medium 11 where they remain stuck. To generate the low pressure in the dish interior, the air is sucked through the air outlet slits 6 into the air suction device 7.

Figure 2:
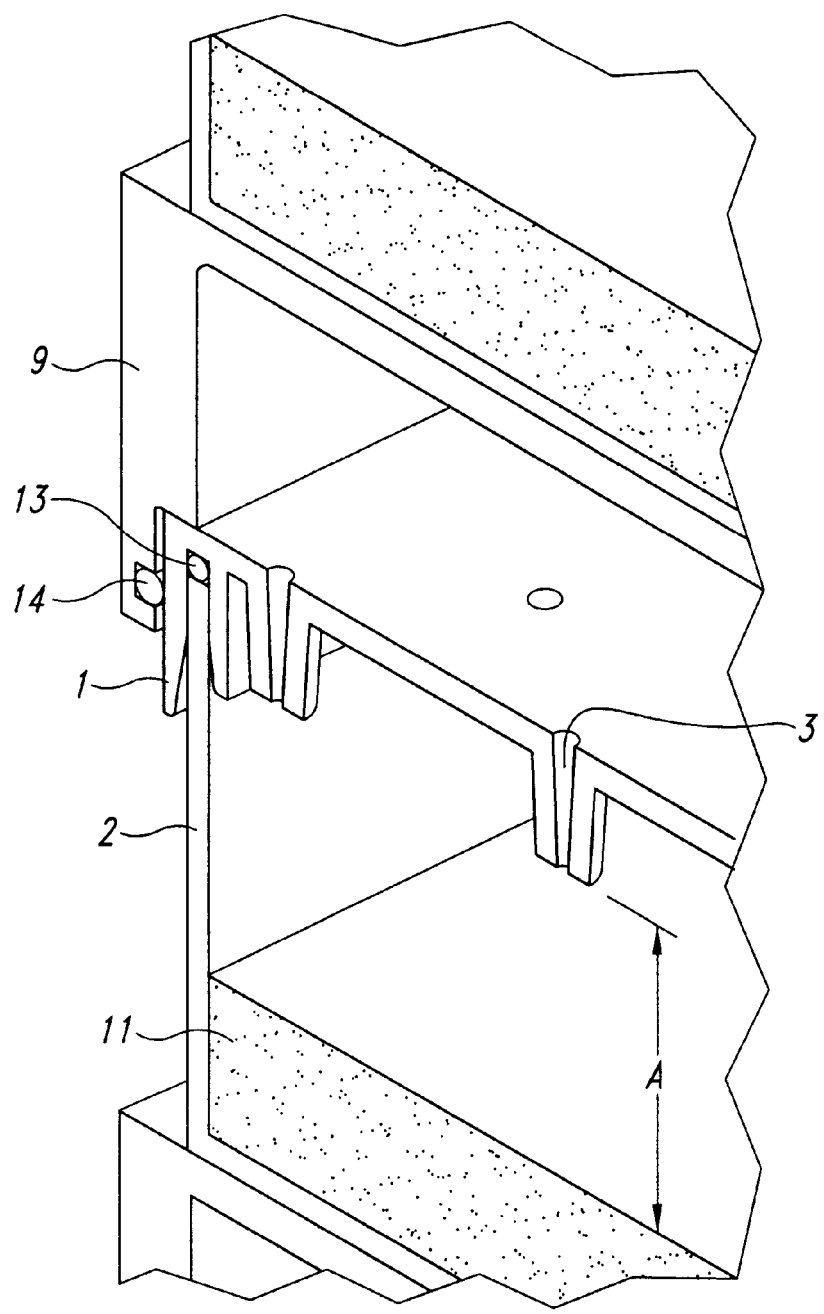
FIG. 2 is a partial representation, in perspective, of a section of culture medium containers stacked on top of one another in a cascade-like way.

FIG. 2 shows a detail of a cascade configuration of culture medium containers according to an embodiment of the invention. Disposed between the dish 2 and the lid 1 of an underlying culture is a cascade connecting hood 9. The cascade connecting hood 9 and the underlying lid 1 form a hermetically sealed chamber, an O-ring 14 being provided on the cascade connecting hood for sealing. In FIG. 2 details of the lid 1 have also been given; in the groove on the edge of the lid 1 there is an O-ring 13, which is responsible for the hermetic seal with the dish 2. Visible in the lid 1 are also the air admission apertures 3, which are designed as conical nozzles. Simple holes in the lid 1, however, are also suitable for the purpose. Well visible is also the impaction distance A between the nozzle end and the culture medium 11.

Figure 3:
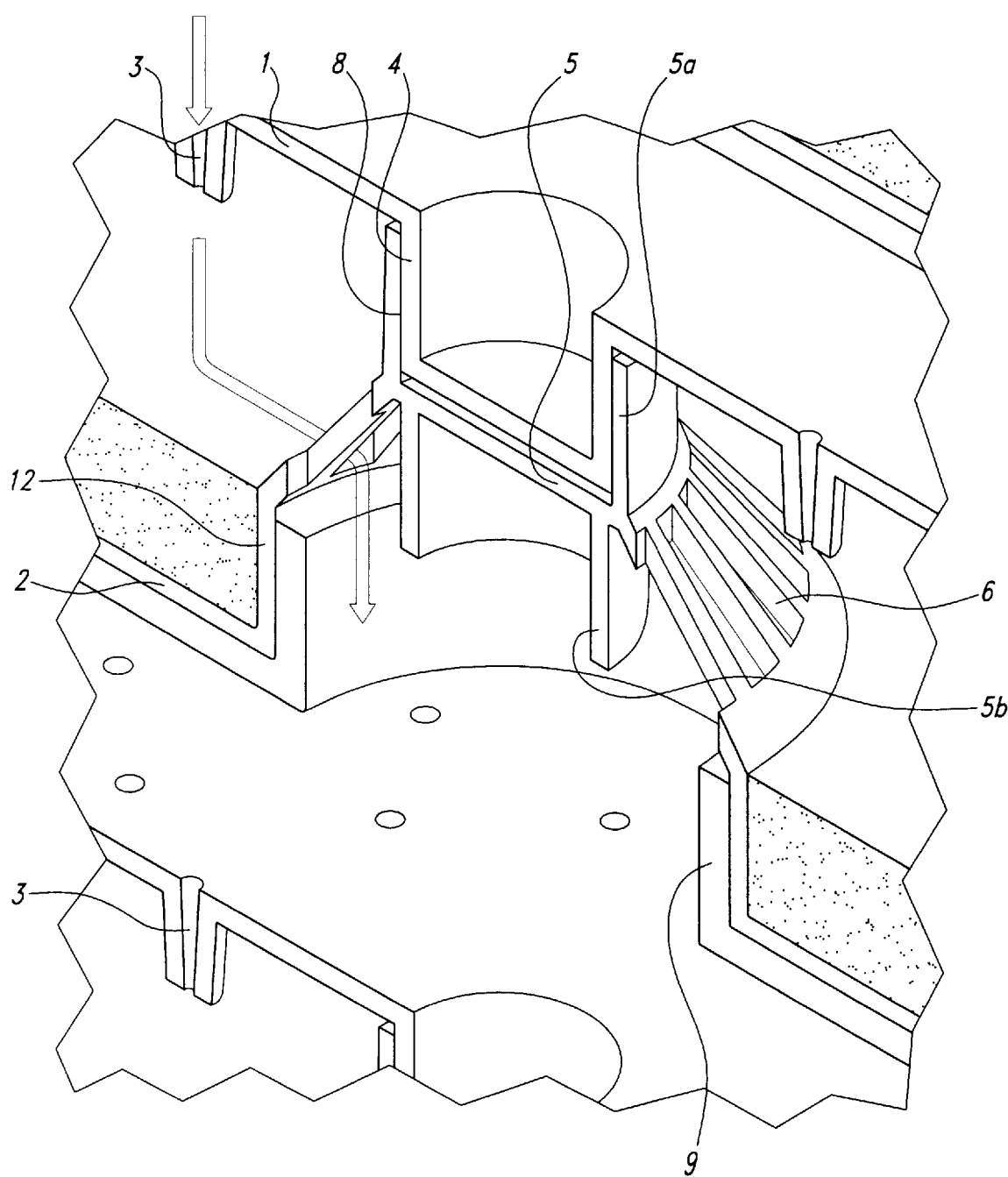
FIG. 3 is a partial representation, in perspective, of a section of culture medium containers stacked on top of one another in a cascade-like way, the air conduction geometry being central.

FIG. 3 is a partial view of a cascade configuration of two culture medium containers according to an embodiment of the present invention, with a cascade connecting hood 9 situated between them. The cascade connecting hood 9 has in the center an opening coming out into a hollow cylinder, which fits into the protuberance 12 of the dish 2 while forming an airtight connection. Clearly visible is the recess 4 of the lid 1, which forms a conical plug-in connection 8 with the upper connecting socket 5a of the central part 5 of the protuberance 12. Clearly visible in this partial view is the airstream, designated by arrows, which reaches from the air admission aperture 3 of the lid 1 into the culture medium container to the culture medium 11, and from there into the interior of the cascade connecting hood 9, via the air outlet slits 6. Afterwards, the air (not indicated in the illustration) is led into the air admission apertures 3 of the lid 1 of the underlying culture medium container. Such a cascade configuration can comprise, for example, three culture medium containers, which are connected to two cascade connecting hoods 9. It is thereby possible for the air admission apertures 3 of the lid 1 of the different culture medium containers to be of differing size. This requirement results from current test regulations.

Figure 4:
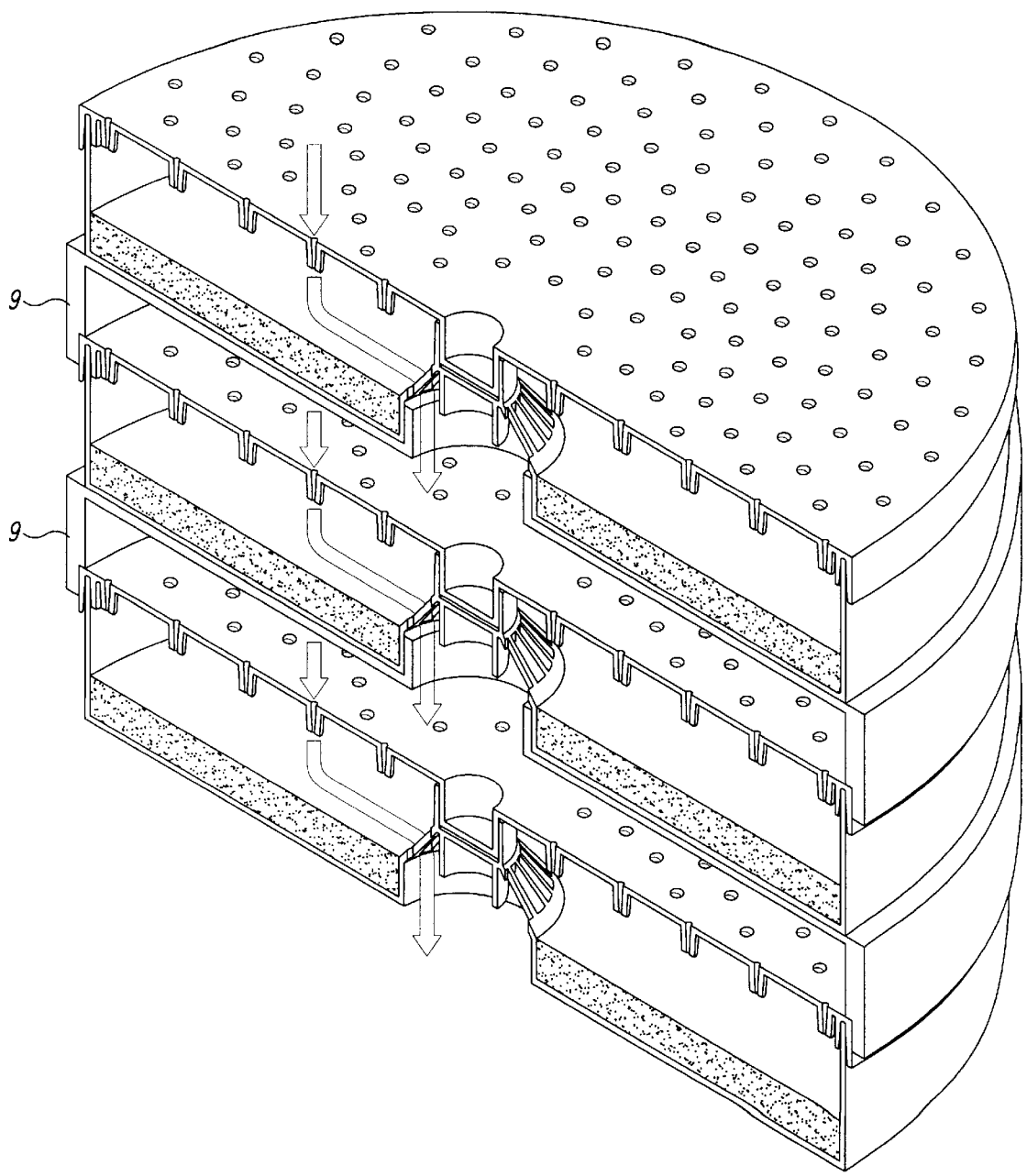
FIG. 4 is a representation, in perspective, of a section of culture medium containers stacked on top of one another in a cascade-like way with cascade connecting hoods situated between them.

Shown in FIG. 4 is a view, in perspective, of a cascade configuration of three culture medium containers with cascade connecting hoods 9 situated between them. Well visible is the stream of air represented by arrows.

Figure 5:
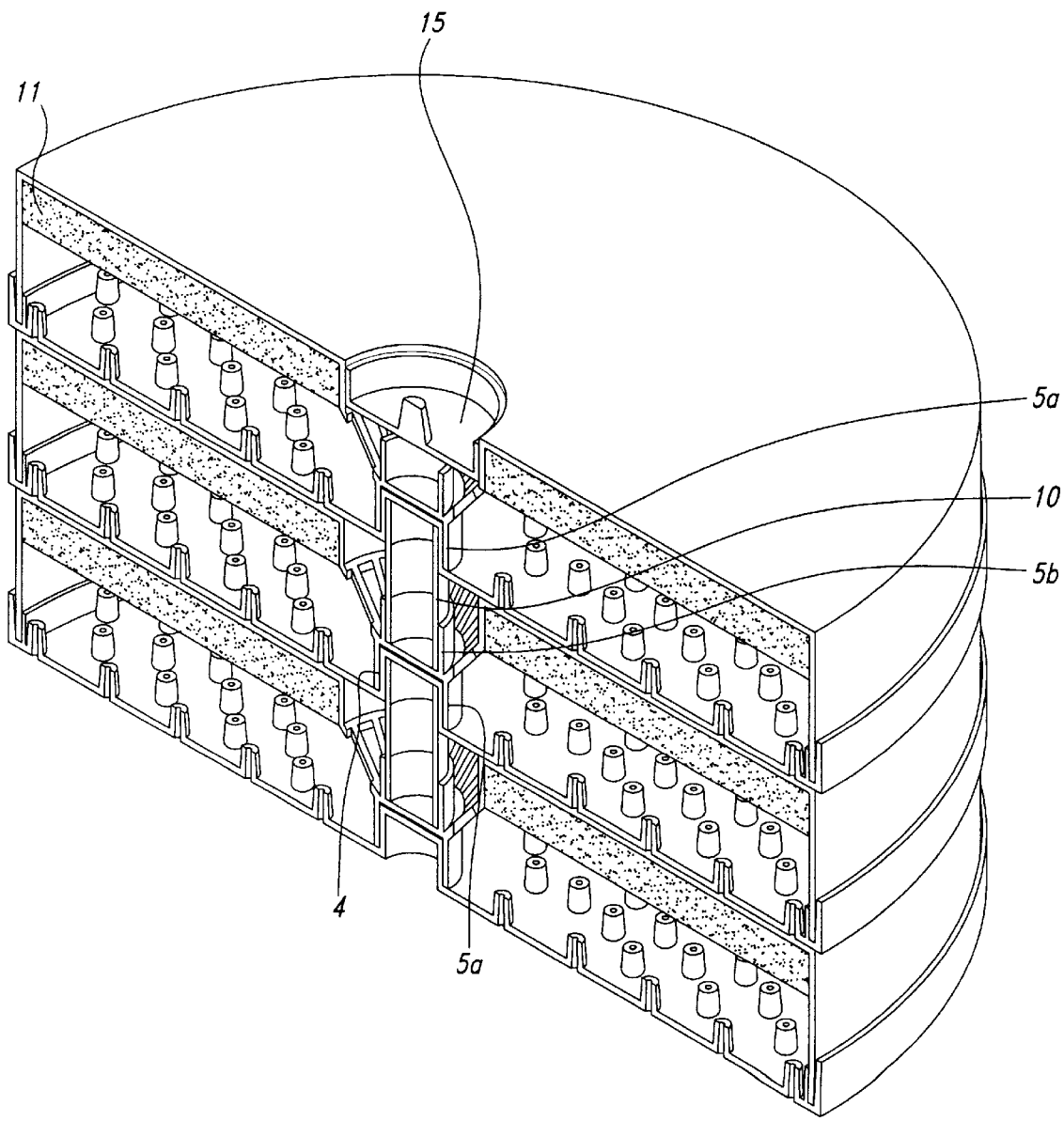
FIG. 5 is a representation, in perspective, of a stack of containers with a section along the central axis.

FIG. 5 shows a stack, upside down, of three culture medium containers according to another embodiment of the invention without cascade hoods. Such an arrangement is useful, for example, when supplying culture medium containers already containing a culture medium 11. This configuration can also be used for the incubation following passage of the prescribed quantity of air. A special feature of this stack are the spacers and connecting means in the form of connecting pegs 10 between the blind hole of the lower connecting socket 5b and the recess 4 of the lid 1. Depending upon the length of these connecting pegs 10, a larger or smaller air gap, or no air gap at all, can result between the individual culture medium containers. The peg 15 is provided for hermetic sealing of culture medium containers. Contamination, by the surrounding air, of the sterile inner contents of the culture medium container is thereby prevented. To achieve this, the culture medium containers must be stacked without interim space.

What is claimed is:

1. A culture medium container for air bacteria analysis according to the impaction method, comprising a dish and a fitted lid, the culture medium container having an integrated geometry with respect to air suction and air conduction in the form of apertures in the lid and dish, the dish having a central protruberance projecting from a dish bottom, and at least one of the apertures in the dish being located on the protuberance.

2. The culture medium container according to claim 1, wherein the lid fits on the dish in such a way that a hermetic seal is formed so that air admission is possible only through the apertures provided for that purpose.

3. The culture medium container according to claim 1, wherein a conical plug-in connection is provided for a mechanically stable connection between the lid and the dish.

4. The culture medium container according to claim 1, wherein the lid fits on the dish in such a way that a hermetic seal is formed so that air admission is possible only through the apertures provided for that purpose, a conical plug-in connection is provided for a mechanically stable connection between the lid and the dish, the lid is provided with air suction apertures, and the dish has a central protuberance, directed upward from the dish bottom, with air outlet apertures.

5. The culture medium container according to claim 4 wherein the central protuberance of the dish has a central part having a connecting socket directed upward with respect to the dish interior, with a conical blind hole, and the corresponding lid has a conical recess which fits into the blind hole, forming a conical plug-in connection, and the air outlet apertures of the protuberance are disposed substantially symmetrically around the central part.

6. The culture medium container according to claim 5, wherein provided on the central protuberance of the dish is a downwardly directed connecting socket for a further conical plug-in connection, which allows a stable stacking of a plurality of successive culture medium containers with or without interim gap between dish and lid.

7. The culture medium container according to claim 6, wherein provided, as a spacer, for the further conical connection is a connecting peg which engages one of the blind hole and the recess of the lid, the spacing between dish and lid of successive containers being controlled by means of the length of said connecting peg.

8. The culture medium container according to claim 1, wherein the lid is provided with air suction apertures of a predetermined size for the purpose of differentiating according to particle size.

9. The culture medium container according to claim 1 wherein the dish and lid are designed in such a way that a plurality of such culture medium containers can be stacked one upon another.

* * * * *